United States Patent [19]

Chick

[11] Patent Number: Plant 5,508

[45] Date of Patent: Jul. 9, 1985

[54] APPLE TREE

[75] Inventor: Norman A. Chick, Monmouth, Me.

[73] Assignee: James L. Glazier, Monmouth, Me.

[21] Appl. No.: 487,051

[22] Filed: Apr. 21, 1983

[51] Int. Cl.[3] ..... A01H 5/03

[52] U.S. Cl. ..... Plt/34

[58] Field of Search ..... Plt./34

*Primary Examiner*—Robert E. Bagwill

*Attorney, Agent, or Firm*—Frank B. Robb

[57] ABSTRACT

A variety of apple tree of the McIntosh strain, being a full genetic dwarf which even after years of growth maintains short height, the crotch angles of the branches being consistently between 72 and 90 degrees with these angles being maintained without training, the intervals between nodes being consistently short and identifying the tree as a spur-type, propagation on seedling or other rootstock being successful for excellent anchorage, adaptability to a wide range of soil conditions being a very important consideration, the fruit being typical of the Rogers' red McIntosh without any tendency to striping.

1 Drawing Figure

DESCRIPTION OF THE INVENTION

The present invention relates to a new and distinct variety of Apple Tree which was discovered by me as a whole-tree sport of what is known as the "Rogers McIntosh", which latter tree, is unpatented and was discovered and has since been propagated by Issac C. Rogers of Dansville, N.Y.

The Rogers' McIntosh produces a dark red strain of McIntosh apples which are uniformly colored a solid dark red. The fruits of the Rogers' McIntosh do not differ from the ordinary McIntosh otherwise, and the same is true of the variety of my present invention.

The primary advance provided by my discovery and propagation, which is also here identified as "Chic-A-Dee" McIntosh, is that it is distinguished from prior McIntosh trees and specifically the Rogers' McIntosh trees and other adjacent McIntosh trees by its small size approximately half the size of adjacent McIntosh trees of the same age, and other characteristics which are particularly outstanding including the spur-type habit of growth, short internodes and heavy spur development, together with the fact that the tree is very productive.

In fact the tree may be described as a full genetic dwarf in that it is about nine feet high years after its original development.

Since the fruit is substantially like that of the Rogers' McIntosh referred to and cannot normally be distinguished therefrom, it is not described as part of the invention, the primary aspects hereof which are important being the characteristics of the tree which may be summarized by the following:

1. It is a full genetic dwarf that is about nine feet high when of substantial age on standard root stock.

2. Crotch angles are consistently between 72 degrees and 90 degrees. The variety of my invention has developed these angles with absolutely no training.

3. Interval between nodes is consistantly short. This contributes to the spur-type characteristic.

4. My new variety has been propagated on seedling or MM111 rootstock for excellent anchorage. These combinations adapt to a wide range of soil conditions.

5. Color is typical of the Roger's McIntosh (unpatented) with no tendency to striping.

In addition to the foregoing specific characteristics of the tree of my invention of this variety, there are obviously certain economic advantages which arise from the foregoing, including those which may be enumerated in the following manner.

a. Pruning has been minimal over the life of my new variety of apple tree.

b. The harvesting is substantially easier because of the lower height.

c. Spray coverage is effective since smaller equipment may be used.

d. The dollar return per acre is substantially greater than the same for larger and taller trees.

e. Tree training is not required and if it is in any respect it is very minimal.

f. The tree adapts for medium or high density plantings to obtain maximum yields on minimal amount of land.

It might be noted in summary that the tree is considered to be a small tree and may be compared with adjacent McIntosh by being stated as about half the size thereof where trees are the same age, and since the branching of the tree is more horizontal than branches of adjacent trees it is obviously easier to effect picking.

It is interesting to note that trees topworked with scions from the tree of my new variety exhibit the spur-type habit of growth, fruitfulness and branching thereof, indicating that the characteristics of the tree are reproducible by asexual reproduction. Asexual reproduction has also been carried out by me in an orchard in which the tree of my new variety was originally grown and in an orchard in the area of Winthrop, Maine, and specifically the York Block therein.

It also should be noted that my new variety has been asexually reproduced by budding and that it does in fact come true in successive asexual reproductions.

General characteristics of the tree of my new variety are the most important and a tree exemplary of my new variety is shown in the accompanying drawing in color as near as possible to reproduce in an illustration of this kind. Since colors of the various parts of the tree and fruit of my new variety are not distinctive from the Rogers' McIntosh, they are not referred to in comparison with a color chart, where color is mentioned, it is in the ordinary dictionary sense, since the fruit thereof and the tree itself are of the same colors and characteristics in any event.

However, I have set forth hereinafter the specific characteristics by which the tree can be identified in other respects than color noting that it is generally a vigorous, round, spreading tree with numerous small laterals and hardy in nature.

The enumerated characteristics are those which are distinctive and make the tree identifiable as distinct from other trees of similar nature and specifically of course though related to the Rogers' McIntosh, the small size of most of the aspects of the tree of my new variety being distinctive in itself.

The tree illustrated in the drawing is exemplary of the tree of my new variety and as such a true genetic dwarf in this case being about nine feet high having been planted in 1968.

Locality where grown and observed: Winthrop, Maine.

Tree: Large; vigorous; spreading; tall; round; rapid growing; hardy; very productive; regular bearer.

*Trunk.*—Medium; medium smooth.

*Branches.*—Medium; slender; medium smooth; many; reddish to reddish olive in color. Lenticels — Medium in number; medium in size.

*Leaves.*—Large to medium in size; wide to medium width; long to medium in length; broad to oval; abruptly pointed; thick to medium; dark green; smooth to rugose.

*Leaves.*—Margin — Crenate. Petiole — Short; thick to medium.

FRUIT:

*Form.*—Uniform; symmetrical; globose; oblate.

*Cavity.*—Symmetrical; acuminate; occasional russetting.

*Basin.*—Symmetrical; abrupt; narrow.

*Stem.*—Slender to medium; length — 0.5 inch.

*Calyx.*—Segments persistent.

*Eye.*—Small; partially closed.

*Skin.*—Thin; tough; smooth; glossy; dots obscure; many; small; even; circular; dots white with even distribution; ground color pale yellow; Bloom — Abundant; wanting. General color effect — Red, as in parent variety.

Flesh: Juicy; white.

*Texture.*—Tender; fine; crisp.

*Flavor.*—Subacid; sprightly; aroma pronounced; quality best.

Core: Medium sessile.

*Calyx.*—Urn-shaped.

I claim:

1. A new and distinct variety of apple tree, substantially as herein shown and described, characterized particularly as to novelty by the unique combination of dwarf size and maintenance of that size throughout its productive life, crotch angles between 72 and 90 degrees consistently, little or no training being required to maintain such crotch angles, short intervals between nodes, ability to propagate on seedling and certain rootstocks for excellent anchorage, adaptability to wide range of soil conditions and the production of fruit which is typical of the red McIntosh known as Rogers, the tree being vigorous, round and spreading with small laterals, and hardy.

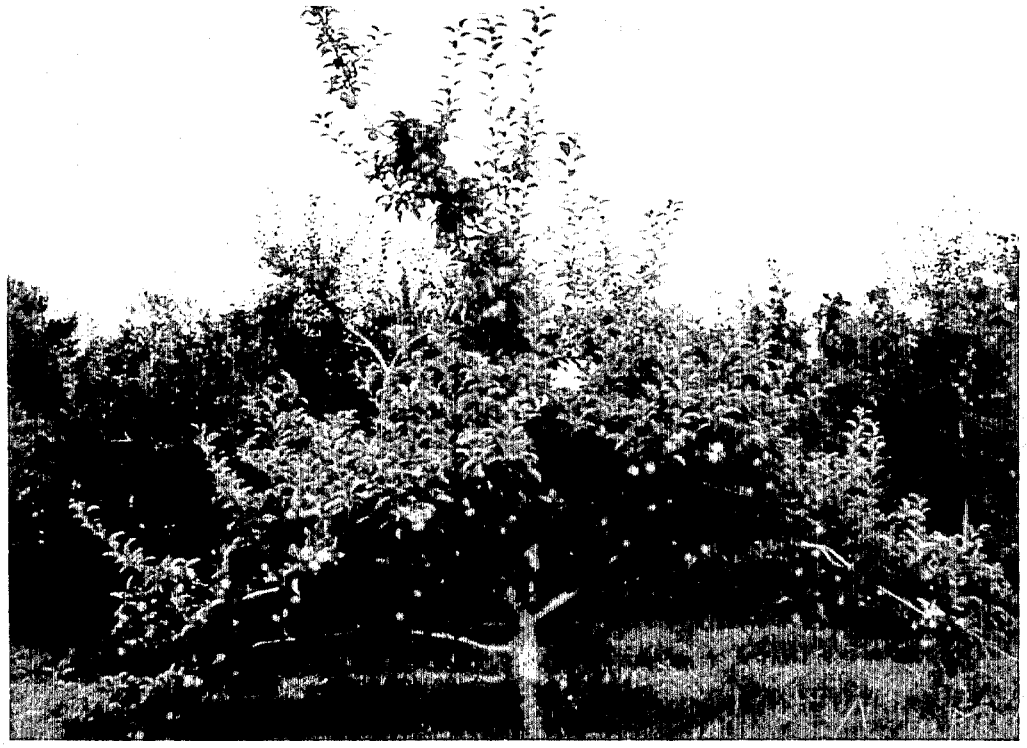

* * * * *